(12) United States Patent
Reynolds

(10) Patent No.: US 11,026,692 B2
(45) Date of Patent: Jun. 8, 2021

(54) DEVICE AND SYSTEM FOR RESTRICTING FLUID FLOW IN PHYSIOLOGICAL VESSELS

(71) Applicant: Elbe Valley Medical Ltd., County Westmeath (IE)

(72) Inventor: Rob Reynolds, Vellberg (DE)

(73) Assignee: Elbe Valley Medical Ltd., Co. Westmeath (IE)

( * ) Notice: Subject to any disclaimer, the term of this patent is extended or adjusted under 35 U.S.C. 154(b) by 41 days.

(21) Appl. No.: 16/081,136

(22) PCT Filed: Feb. 8, 2017

(86) PCT No.: PCT/EP2017/052760
§ 371 (c)(1),
(2) Date: Aug. 30, 2018

(87) PCT Pub. No.: WO2017/153114
PCT Pub. Date: Sep. 14, 2017

(65) Prior Publication Data
US 2019/0021740 A1   Jan. 24, 2019

(30) Foreign Application Priority Data
Mar. 9, 2016 (GB) .................................. 1604074
Nov. 22, 2016 (IE) .................................. 2016/0261

(51) Int. Cl.
*A61B 17/12* (2006.01)
(52) U.S. Cl.
CPC .... *A61B 17/12109* (2013.01); *A61B 17/1204* (2013.01); *A61B 17/12022* (2013.01); *A61B 17/12031* (2013.01); *A61B 17/12036* (2013.01)

(58) Field of Classification Search
CPC ........ A61B 17/12022; A61B 17/12031; A61B 17/12036; A61B 17/1204; A61B 17/12109
See application file for complete search history.

(56) References Cited

U.S. PATENT DOCUMENTS

| 4,471,779 A | * | 9/1984 | Antoshkiw ...... A61B 17/12109 604/907 |
| 2007/0156211 A1 | * | 7/2007 | Ferren ................ A61B 5/02007 607/101 |

(Continued)

FOREIGN PATENT DOCUMENTS

| EP | 1169969 A1 | 1/2002 |
| WO | 2012138144 A2 | 10/2012 |

OTHER PUBLICATIONS

International Search Report received in PCT/EP2017/052760 dated May 17, 2017.

(Continued)

*Primary Examiner* — Melanie R Tyson
(74) *Attorney, Agent, or Firm* — Suzannah K. Sundby, Esq.; Canady + Lortz LLP

(57) ABSTRACT

Provided is a device and system for restricting fluid flow in physiological vessels of humans or animals, the device being configurable in a first mode to be passively propellable by fluid flow within a physiological vessel and in a second mode to at least partially occlude a physiological vessel, the device having a first cross-sectional size in the first mode and a second cross-sectional size in the second mode, wherein the second cross-sectional size is greater than the first cross-sectional size. The system has a plurality of the devices described above, a power source for powering the devices; and a controller having one or more processors for controlling the devices.

19 Claims, 15 Drawing Sheets

(56) References Cited

U.S. PATENT DOCUMENTS

2008/0241264 A1    10/2008  Solomon
2009/0192209 A1     7/2009  Mahoney et al.
2011/0048433 A1     3/2011  Pfister

OTHER PUBLICATIONS

Written Opinion received in PCT/EP2017/052760 dated May 17, 2017.
Combined Search and Examination Report received in GB1604074.3 dated Aug. 18, 2016.
Written Opinion received in SG 11201807701X dated Nov. 26, 2019.

* cited by examiner

DEVICE AND SYSTEM FOR RESTRICTING FLUID FLOW IN PHYSIOLOGICAL VESSELS

FIELD

The present invention is related to a device and system for restricting fluid flow in physiological vessels of humans and animals.

BACKGROUND OF THE INVENTION

The overriding problems in treating tumours and cancers in particular using current methods are threefold. Chemotherapy works well for small tumours but once a tumour reaches a certain size it tends to grow faster than the treatment can slow it. Chemotherapy is difficult for patents due to the side effects of the drugs used. Radiotherapy has a similar drawback albeit with fewer side effects arguably. Surgery is often not feasible due to the location of the unwanted tissue. Current technology is not adapted to treatment of fast growing tumours or indeed unwanted human tissues and currently for patients with advanced stage cancers the current strategy is to use the above-mentioned methods to try to slow the progress of the disease and lengthen the quantity of the patient's life. Often however the patient suffers greatly and experiences a lot of discomfort.

The treatment of tumours, lesions and other unwanted tissues in humans and animals using the above-mentioned methods causes side effects due to the inability of the treatment to completely isolate the targeted tissue (be it a tumour, lesion or other unwanted tissue) from healthy tissue.

In the case of chemotherapy, drugs are administered to the patient in large doses to prevent the spread of cancer and to eliminate the tumour in the process. However as the entire body is exposed to the active chemicals of the drug, side effects are almost unavoidable.

In the case of radiotherapy, the patient has his/her tumour imaged using an MRI scanner and the treatment is carried out (usually) by applying focused radiation on the tumour, the radiation being generated by a linear accelerator with a beam which comes into focus at the point in the body where the tumour is located. As the beam is delivered to the tumour over as wide an angle as possible, the dose to the normal tissue is kept as low as possible. Radiotherapy still has side effects such as skin burning.

Both chemotherapy and radiotherapy are effective on smaller tumours. If a tumour reaches a critical mass it is able to grow at a higher rate than either chemotherapy or radiotherapy can destroy. When this happens, these treatments are used to slow the rate of progress of the cancers only.

Surgery is also used to reduce tumour size. However surgery is invasive and often not feasible due to the location of the tumour. The overriding problems in treating illnesses where the removal of unwanted tissue is desirable, is with the ability of current technology to differentiate between wanted and unwanted tissue.

Current technology is not adapted to treatment of fast growing tumours or indeed unwanted human tissues and currently for patients with for example; advanced stage cancers and other such illnesses. Current treatment relies heavily on the use of drugs and where feasible surgery to destroy unwanted tissues. These methods have several drawbacks such as unwanted side effects and in many cases the patient with the disease suffers greatly.

One of the methods used to image a tumour is a commercially available Magnetic Resonance Imaging (MRI) machine which is used widely in medicine to diagnose abnormalities with human bone and tissue and this technology is used mainly as a diagnostic tool. MRI imaging is discussed further below.

The human body contains approximately 10 billion blood capillaries with an average length of 1.1 mm. Capillaries are the smallest of a body's blood vessels (and lymph vessels) that make up the microcirculation. Their endothelial linings are only one cell layer thick. These microvessels, measuring around 5 to 10 micrometres ($\mu$m) in diameter, connect arterioles and venules, and they help to enable the exchange of water, oxygen, carbon dioxide, and many other nutrients and waste substances between the blood and the tissues surrounding them, as illustrated in FIG. 1.

Blood flows from the heart through arteries, which branch and narrow into arterioles, and then branch further into capillaries where nutrients and wastes are exchanged. The capillaries then join and widen to become venules, which in turn widen and converge to become veins, which then return blood back to the heart through the great veins.

Capillaries do not function on their own, but instead in a capillary bed, an interweaving network of capillaries supplying organs and tissues, as illustrated in FIG. 1. The more metabolically active a cell or environment is, the more capillaries are required to supply nutrients and carry away waste products. Capillary beds can comprise two types of vessels: true capillaries, which branch from arterioles and provide exchange between cells and the blood, and short vessels that directly connect the arterioles and venules at opposite ends of the beds, metarterioles, only found in the mesenteric circulation.

Cancers and other tumours create hormones to promote the development of new blood vessels using a process called vasculogenesis. It is by this process that the new tissue can acquire the nutrients and oxygen needed as well as the disposition of cellular waste matter. The functioning of a tissue's capillary system is central to the tissue's ability to live.

Nanorobots have been hailed as a potential solution to the treatment of diseases such as cancer by being designed to deliver a drug directly to the site of a cancer tumour without affecting the surrounding healthy tissue. There are a number of issues with previous nanorobot designs that have limited the usefulness of nanorobots in treating disease.

Previous designs incorporated onboard sensors to detect the target tissue, which adds to the cost and complexity to the design. The sensors and processing capability to correctly detect the target tissue make it difficult to ensure accuracy of efficacy of the treatment prior to the commencement of treatment. Also it is difficult to guarantee that the nanobots have delivered their dose in the right location, which necessitates a complex feedback system from the devices to discover how the treatment went. As a result, real-time control of the nanobots can be difficult to achieve.

Nanorobots usually consist of a propulsion mechanism to enable them to move around the body usually mimicking bacterial flagella in order that they might reach the targeted tissue. There are currently several ways of powering nanorobots at present, including ultrasonic energy transfer, microwaves or magnetic fields.

Currently in the medical diagnostic field, three-dimensional imaging may be achieved using three methods as outlined below.

Magnetic Resonance Imaging (MRI)
Computed tomography (CT scan)
Ultrasound

Magnetic Resonance Imaging (MRI) has proven to be an excellent diagnostic tool. It utilizes strong magnetic fields, radio waves, and field gradients to form images of the body. Some of the drawbacks to this technology however include (1) high capital cost of equipment, (2) high running costs, (3) long data processing times to obtain images from the raw data, (4) the patient must remain completely still during the scan which can be up to 20 minutes, and (5) real-time data from the patient is not possible; therefore, it is not possible to capture fast moving data such as the opening and closing of a heart valve.

Computed Tomography (CT) is another high quality diagnostic tool; however, it shares almost all of the drawbacks mentioned above plus some more; (1) it uses ionizing radiation, thereby increasing the patient's exposure with every scan, (2) High contrast imaging requires the use of higher exposure doses, and therefore the doctor must decide between high quality imaging and patient exposure. For diagnostic purposes the doctor would wish to have the dose as high as possible to obtain the best quality image. However should she decide on using a lower dose to protect the patient and later finds that the quality of the image is poor, she must subject the patient to another scan and to a higher overall dose than if she chose a high quality image in the first place.

Ultrasound has been used for diagnostics for many years and is well established as being a low risk way of obtaining diagnostic data. Another advantage of ultrasonic imaging is that the image can be generated in real time and can be used to diagnose dynamic tissues such as heart valve diagnostics. Ultrasonic imaging however has not been without its disadvantages among which are: (1) unwanted reflections from inside the subject's body, (2) difficulty achieving focus at the intended location, (3) low resolution images, and (4) unsuitable for use on soft tissues without injecting the patient with an ultrasonic contrast medium, which as already described, can cause tissue cavitation.

As already discussed, traditional imaging systems are limited in the way they process information. Take for example a microscope lens. The numerical aperture of a microscope objective is a measure of its ability to gather light and resolve fine specimen detail at a fixed object distance. FIG. 1 is a drawing that illustrates the limitation of numerical aperture in traditional imaging systems. In FIG. 1 for example the numerical aperture can be calculated as follows.

$$N.A.=n \times \sin \theta$$

Where n is the index of refraction of the medium and θ is the maximal half-angle of the cone of the wave that can enter or exit the imaging device.

In traditional imaging systems, illuminating waves (light waves in the case of CT and ultrasonic waves in the case of ultrasound) are used to illuminate the target. These waves diffract against the target meaning the incoming wave impacts the target and causes diffraction orders to be generated. These orders are gathered by the imaging system to form an image of the target. Zero order diffraction order contains very much energy but no information about the target. Higher diffraction orders contain less energy but more information about the target. Higher diffraction orders travel at a given angle from the zero order meaning the higher the diffraction order, the higher the angle it has and the higher the resolution of the imaging system can be achieved. Also notable here is the fact that higher orders due to the angular component have a longer path from where they are generated to the receiving mechanism. Many ultrasonic devices use this property called "time-of-flight" to differentiate between usable information from the target and noise.

In traditional ultrasonic diagnostic devices, the ultrasound is generated and received by a handheld transducer that the operator moves as she wishes. This limits the resolution of the image obtained since the ability to detect higher diffraction orders are limited by the physical size of the transducer. As a result, handheld ultrasonic diagnostic devices must detect lower orders and be subjected to the unwanted effects of the zero order reflections.

In view of the above, there is a need for a means for quickly and accurately destroying unwanted tissue in humans and animals without the side effects commonly associated with other methods.

SUMMARY

According to the present disclosure there is provided a device as detailed in claim 1. Also provided is a system in accordance with claim 22. Advantageous features are claimed in dependent claims.

The present disclosure provides a device and system for accurately restricting fluid flow such as the flow of blood in physiological vessels of humans and animals. The device will hereinafter be referred to as a nanorobot or a nanobot. A nanobot may comprise a mechanical or electromechanical robot small enough to pass through the human or animal circulatory system. The nanobot of the present disclosure may have a cross-sectional size in a range of about 2.8 µm to about 5.2 µm in an unactivated state.

The nanobot may be fabricated using standard semiconductor or MEMS (Micro-Electro-Mechanical Systems) technology. The nanobot may comprise a radio antenna which receives position signals from a primary validation subsystem via an RF encoder/interferometer system. In this manner the nanobot can detect its relative displacement from a fixed starting point in the X, Y and Z axes.

An imaging apparatus, such as an MRI machine, may be used as a separate device but in conjunction with the present disclosure to provide (a) a verification of the existence and location of unwanted tissue and (b) as a power source for the nanobots via a magnetic field.

The purpose of the nanobots is to disrupt the normal operation of the capillary network in the target region in order to destroy damaged or unwanted tissue.

A magnetic flux generating mechanism may be used to provide the power source for the nanobots.

The nanobots may be configured to operate in parallel with external beam radiation devices where an externally produced beam of ionising electromagnetic radiation is used to illuminate the target region. An advantage of this method over conventional radiotherapy is that only a small fraction of the normally applied radiation dose is required since the radiation will be used only to activate the nanobots inside the target region and not to treat tumours directly. This reduces the complexity of the nanobots.

The present disclosure also provides a system for restricting fluid flow in physiological vessels of humans or animals, the system comprising:
 a plurality of the nanobots;
 a power source for powering the nanobots; and
 a controller comprising one or more processors for controlling the nanobots.

The power source may comprise a magnetic flux generating mechanism for powering the nanobots, comprising a plurality of electrically isolated electromagnets, wherein the plurality of devices are powered via a plurality of overlapping magnetic fields which are generated from the electrically isolated electromagnets.

The system may also comprise an external beam radiation device for producing a beam of ionising electromagnetic radiation to illuminate a target region.

The present disclosure also provides an ultrasonic imaging system using an externally produced ultrasonic signal as an illumination source. For example, and in the context of the present disclosure, the nanobots as described above may be used to generate the ultrasonic signal.

The ultrasonic imaging system is configured to convert ultrasonic signals and diffraction orders into an optical image using a network of sensors embedded across the surface of a fabric or other material. This can be referred to as an ultrasonic detection matrix. The ultrasonic detection matrix may be configured to be wrapped around a subject or patient's body so that the sensors are in contact with the outer surface of the subject or patient's body.

The ultrasonic imaging system is configured for measuring ultrasonic signals, which enables detection of waves that propagate parallel to main sensing axes meaning that the half-angle θ is effectively 90 degrees which would make the numerical aperture of the system calculated to be unity (with an n of 1.00 for air).

BRIEF DESCRIPTION OF THE DRAWINGS

The present application will now be described with reference to the accompanying drawings in which.

DETAILED DESCRIPTION OF THE DRAWINGS

Figure 1:
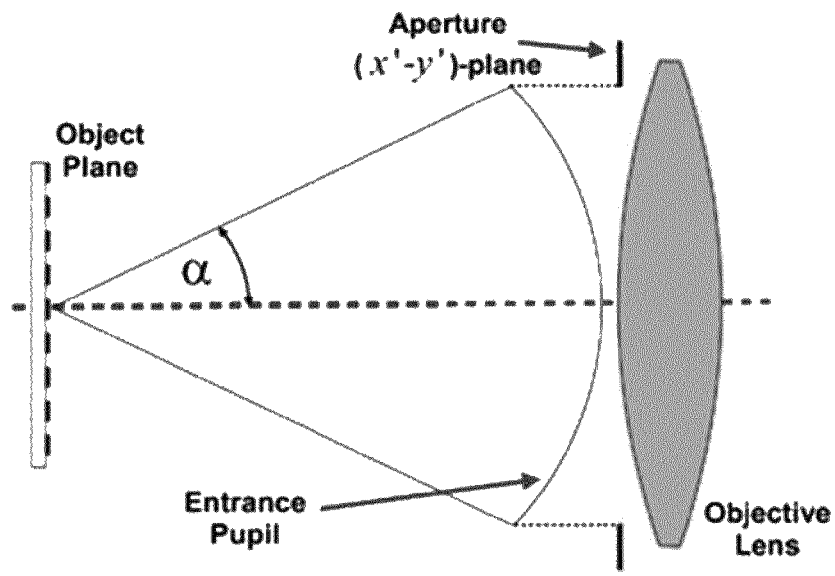
FIG. 1 is a drawing that illustrates the limitation of numerical aperture in traditional imaging systems.

The present disclosure provides a device for restricting fluid flow in physiological vessels of humans and animals. A device for restricting fluid flow in physiological vessels of humans or animals is provided, the device being configurable in a first mode to be passively propellable by fluid flow within a physiological vessel and in a second mode to at least partially occlude a physiological vessel. The device has a first cross-sectional size in the first mode, and a second cross-sectional size in the second mode, wherein the second cross-sectional size is greater than the first cross-sectional size. In order to successfully travel through physiological vessels such as blood vessels, a plurality of nano-sized devices, hereinafter referred to as nanobots may be injected into the subject. For humans, the nanobots may be configured to have a first cross-sectional size in a range of about 2.8 μm to about 5.2 μm in their first mode or unactivated state. The nanobots may be dissolved in an organic solvent to obtain a solution, and the solution may be dispersed in a water-based solvent before being administered to the subject. The nanobots may be injected into the subject while the subject is disposed on an imaging apparatus such as an MRI machine. The nanobots may be carried by the pulmonary system and by the body's natural action to reach all of the capillaries of the body. The nanobots can move freely through the entire pulmonary system while they are not activated. However once they are activated, the nanobots are configured to increase their cross-sectional area thereby inhibiting fluid flow in the blood vessels that they are moving through. The nanobots may be configured to have a cross-sectional size in a range of about 2.8 µm to about 5.2 µm when unactivated. In the context of the present disclosure, the cross-sectional size of the nanobot refers to a cross-sectional diameter or width of the nanobot. At a first cross-sectional size in a range of about 2.8 µm to about 5.2 µm, the nanobots can move freely within the blood vessels of humans. The nanobots may be configured to have a second cross-sectional size of about 7.7 µm to about 14.3 µm when expanded. At the second cross-sectional size of about 7.7 µm to about 14.3 µm, the nanobots may at least partially occlude a human blood vessel. It will be understood however that in other animals, capillary sizes vary and different sized nanobots may be required for treating different animals. The maximum cross-sectional size of a device in its unactivated state may be configured to be approximately 40% of the vessel diameter in the subject human or animal.

Once activated, the nanobots may be configured to expand to obstruct blood flow in the target region. In this regard, the nanobots may have three modes of operation. The first mode is an unpowered and unactivated mode in which the nanobots are sized to freely move through blood vessels. The second mode is a powered and unactivated mode. The third mode is the powered and activated mode in which the cross-sectional area of the nanobots is increased to obstruct blood flow in the target region. In the first and second modes of operation, the nanobots may be configured in the first cross-sectional size described above, i.e., their unactivated size. In the third mode of operation, the nanobots may be configured in the second cross-sectional size described above, i.e., their activated size. The modes of operation will be described further below.

Figure 2:
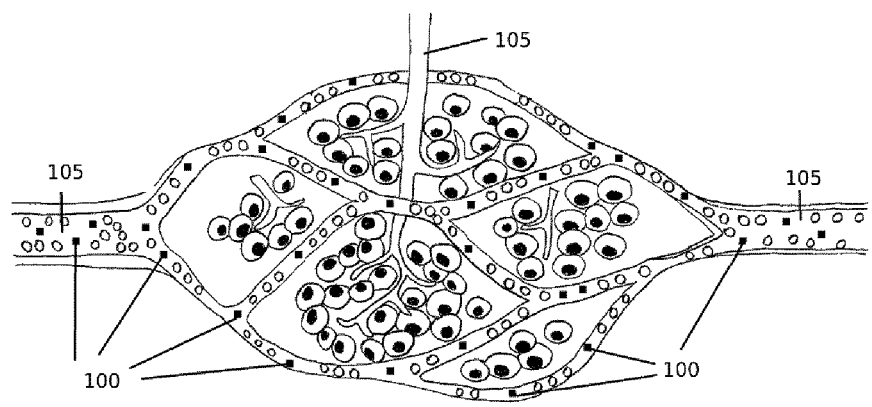
FIG. 2 illustrates nanobots according to an embodiment of the present disclosure as they move through blood capillaries.
Figure 3:
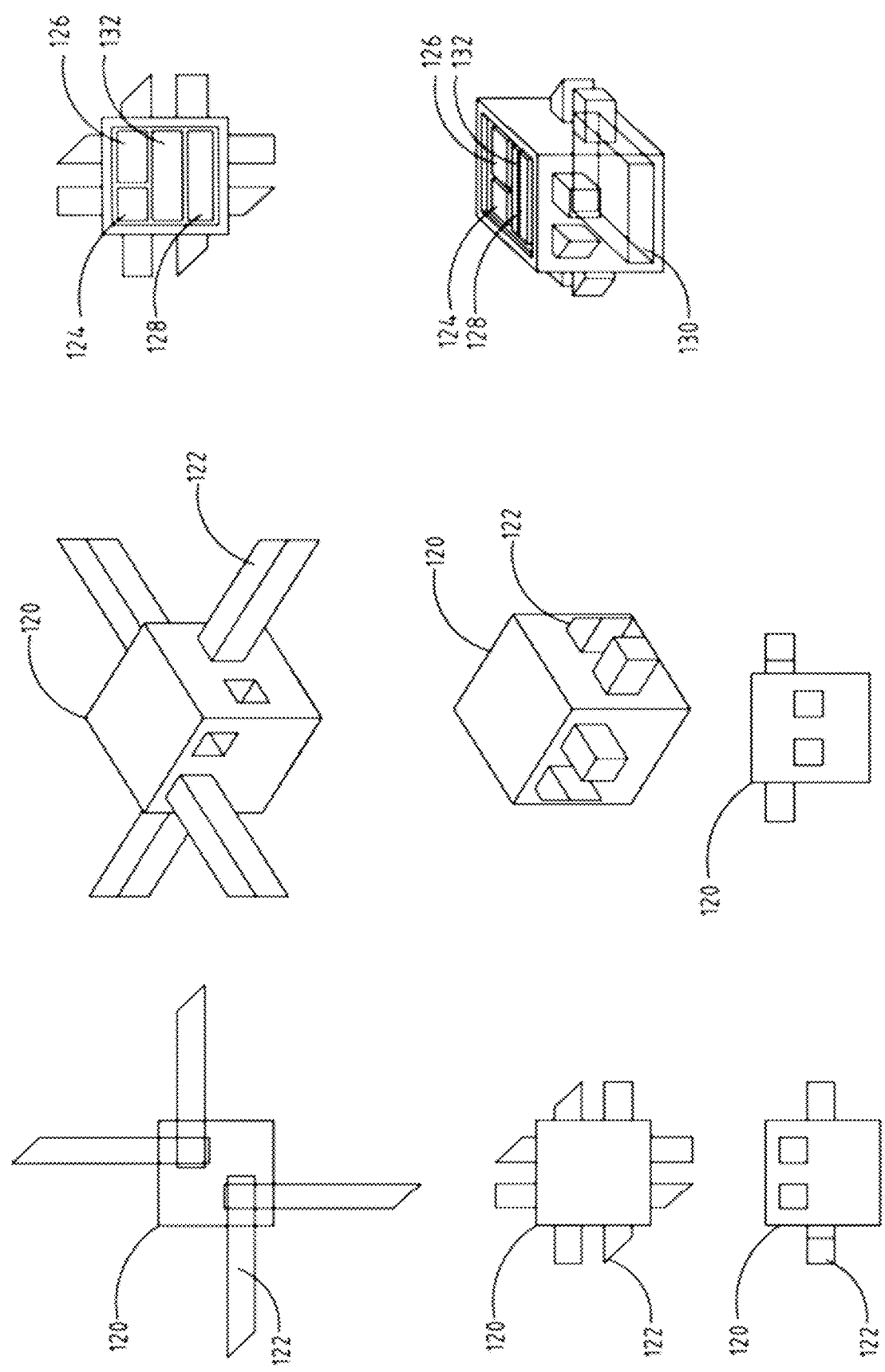
FIG. 3 illustrates various drawings of a nanobot in its unactivated, emitting and expanded states, according to embodiments of the present disclosure.

The nanobot of the present disclosure is a nano-sized device which is small enough to fit through physiological vessels of a human or animal such as blood vessels. Blood vessels include arteries, which carry the blood away from the heart; capillaries, which enable exchange of water and chemicals between the blood and the tissues, and veins which carry blood from the capillaries back toward the heart. FIG. 2 illustrates nanobots 100 according to the present disclosure as they move through blood capillaries 105. Figure illustrates various drawings of nanobots 100 in their various modes, according to an embodiment of the present disclosure. Referring to FIG. 3, the nanobot 100 comprises a main body 120 and one or more extending elements 122 configured to extend from the main body 120 to increase the cross-sectional area of the nanobot 100 when activated. The one or more extending elements 122 may be configured to be housed within the main body 120. The one or more extending elements 122 may be configured to project from outer surfaces of the main body 120. The one or more extending elements 122 may have a planar sheet-like construction. Each of the one or more extending elements 122 may have round or square distal ends to prevent damage to blood vessel walls. The one or more extending elements 122 may project from one or more sides of the main body 120. In FIG. 3, the main body 120 has a parallelepiped shape with planar surfaces but this is merely one embodiment and the present disclosure is not limited thereto. When the one or more extending elements 122 are not extended, the one or more extending elements 122 may be contained within the main body 120. It will be understood that when the one or more extending elements 122 are not extended from the main body 120, the nanobot 100 is in its unactivated state. In this configuration, i.e. the unactivated state, the nanobot 100 can freely pass through blood vessels. However, once the one or more extending elements 122 are activated, the one or more extending elements 122 project from the main body 120 to contact the inner surfaces of the blood vessels. It will be understood that when the one or more extending elements 122 are extended from the main body 120, the nanobot 100 assumes its expanded state. In this configuration, i.e., the expanded mode, the cross-sectional size of the nanobot 100 becomes such that the nanobot 100 can no longer freely pass through the blood vessels. The nanobot 100 may have a first cross-sectional size in a range of about 2.8 µm to about 5.2 µm in the unactivated mode. The nanobot 100 may have a second cross-sectional size of about 7.7 µm to about 14.3 µm in its expanded mode. It will thus be understood that once the one or more extending elements 122 are activated, the nanobot 100 at least partially occludes the blood vessel and obstructs the flow of blood or other fluids within the blood vessel. The nanobot 100 may be configured to at least partially occlude the blood vessel or fully occlude the blood vessel. The nanobot 100 does not have a self-propulsion means as it is configured to be carried in the bloodstream of the patient. Accordingly, the nanobot 100 can be thought of as being passively propelled within the blood vessels by fluid flow. Several million or billion of such nanobots 100 may be administered to the patient to travel around the patient's body by means of the blood circulatory system. The one or more extending elements 122 may be configured to be driven by a micromotor, such as an inchworm motor. The inchworm motor may be a piezo-driven inchworm motor. The micromotor may be housed inside the main body 120.

According to an embodiment of the present disclosure, the main body 120 may comprise a radiation sensitive device such as a transistor or diode to enable the nanobot 100 to be activated. The radiation sensitive device may be a photodiode. The radiation sensitive device may be coated with phosphor or any other such scintillating material. Alternatively, the radiation sensitive device may be a MOSFET of the RADFET variety, or indeed an uncoated diode.

Referring to FIG. 3, the main body 120 may also house a coil 126 for generating the electrical power required to power the nanobot 100. The power may be sourced from a magnetic flux generating mechanism. The nanobots according to the present disclosure remain in an inert unactivated state until they receive power via the coil 126 from the magnetic flux generating mechanism. Embodiments of the magnetic flux generating mechanism are described below and shown in FIGS. 4 and 5.

The energy output of the magnetic flux generating mechanism may be such that only the space where all magnetically generated fields overlap will there be enough energy to power on the nanobots 100.

In the first mode of operation, the nanobots 100 are powered on only and are not activated. To be activated, the radiation sensitive device of the nanobots 100 must detect the presence of ionising electromagnetic radiation. The nanobots 100 of the present disclosure may be configured to operate in parallel with external beam radiation devices where an externally produced beam of ionising electromagnetic radiation is used to illuminate the target region. When ionizing electromagnetic radiation is present, the radiation sensitive device will change state. When the radiation sensitive device changes state, the one or more extending elements 122 may be configured to be activated. In an embodiment, one or more power transistors in the nanobot 100 may be used to activate the one or more extending elements 122. For example, the nanobot 100 may comprise a MOSFET or other similar transistor that is X-ray sensitive.

When the nanobots 100 are powered but no radiation is present, the nanobots 100 may be configured to retract their one or more extending elements 122. This enables the return of blood flow through the target region and to enable reclamation of the devices post therapy.

Referring to FIG. 3, the nanobot 100 may comprise an on-board processor 130 for collecting and processing data. The on-board processor 130 may be configured to activate the one or more extending elements 122. The on-board processor 130 may be an analog data processing unit due to the reduced processing requirements.

Figure 4:
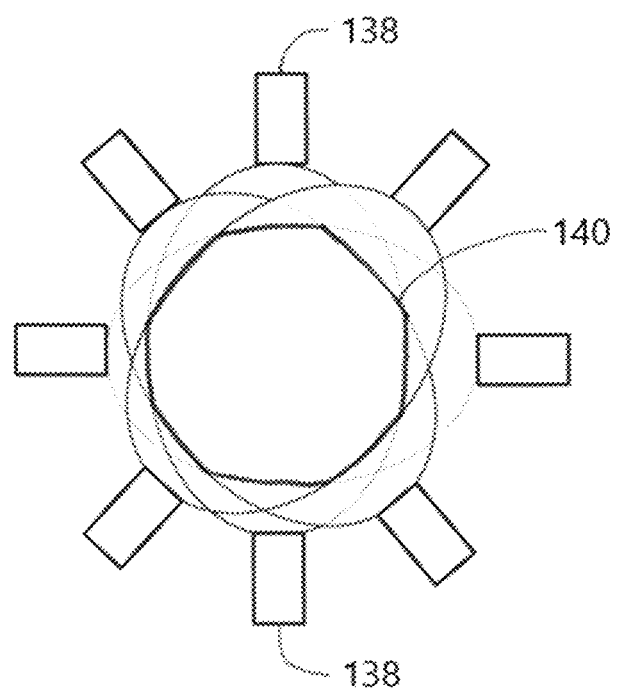
FIG. 4 illustrates a plurality of overlapping magnetic fields which are generated from electrically isolated electromagnets which are placed in an orientation around a patient, according to an embodiment of the present disclosure.

As mentioned above, the nanobots 100 may receive their power via a magnetic flux generation mechanism. The magnetic flux generating mechanism may comprise a plurality of electrically isolated electromagnets which generate a plurality of overlapping magnetic fields. FIG. 4 illustrates a plurality of overlapping magnetic fields which are generated from electrically isolated electromagnets 138 which are placed in an orientation around a patient, according to an embodiment of the present disclosure. The electromagnets 138 may be disposed in an orientation around the patient as illustrated in FIG. 4 but with the central axes of the magnetic flux generating mechanism in proximity to the target area. The electromagnets 138 may be configured to be kept electrically isolated from each other in order to prevent unwanted crosstalk and interference, as would happen if they shared the same power source.

By utilising this method, maximum magnetic flux 140 occurs only in the space where all magnetic fields overlap and flux intensity can be expected to drop off rapidly outside this space. In this manner, the area of maximum flux can be preset at an intensity that power the nanobots 100 inside a defined area (i.e. where all the magnetic fields overlap). In the example illustrated in FIG. 5, four electrically isolated electromagnets 138 are used and maximum magnetic flux 140 is generated where the four magnetic fields overlap.

Figure 5:
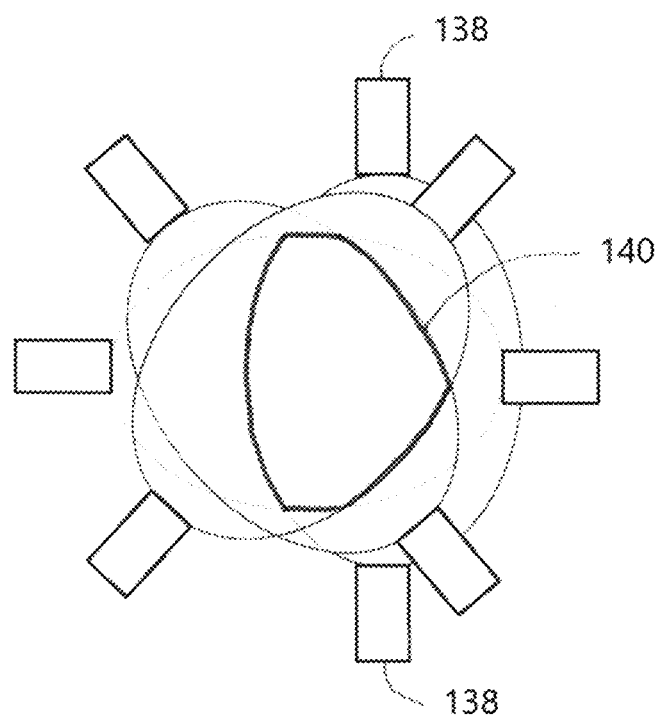
FIG. 5 illustrates the electromagnets being purposely misaligned with respect to the central axes of the magnetic flux generation mechanism, according to an embodiment of the present disclosure.

FIG. 5 shows that the space of maximum flux is adjustable and can be reduced, for targeting smaller tumors for example. By purposely misaligning the electromagnets 138 with respect to the central axes of the magnetic flux generating mechanism, the area of maximum flux 140 may be reduced to as small a size as desired so that it is possible to perform a setup so that the volume of the magnetic field is matched closely to the volume of the target region.

Both FIGS. 4 and 5 illustrate a 2-dimensional (2D) arrangement of the electromagnets 138. However this is only for illustrative and clarity purposes. In another embodiment, the magnetic flux generating mechanism may have electromagnets arranged in a 3-dimensional (3D) configuration and the space of maximum flux may be adjustable in three dimensions.

The 3D configuration may increase patient safety quite drastically while also creating the potential for more accurate targeting. Currently, external beam radiation devices have a targeting accuracy in the millimeter range. However combined with the magnetic flux generating mechanism as outlined here, it is possible to reduce that further. In the event of misalignment or mishandling, the wrong tissue may not be destroyed due to the fact that the very low intensity external radiation beam and the magnetic field need to be in the same place. The only situation where a patient would be harmed is if both the external beam radiation device and the magnetic flux generator were both purposely targeted on the wrong location simultaneously.

The present disclosure also provides a system for restricting fluid flow in physiological vessels of humans or animals, the system comprising:

a plurality of the nanobots 100 described above;

a power source for powering the nanobots 100; and a controller comprising one or more processors for controlling the nanobots 100.

Figure 6:
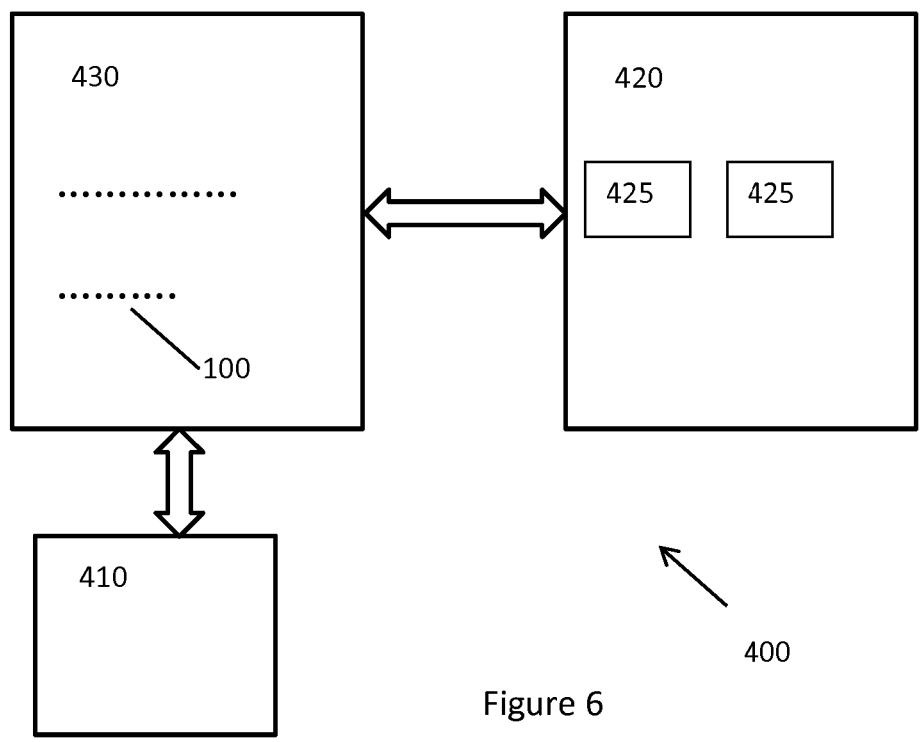
FIG. 6 is a block diagram illustrating a system for restricting fluid flow in physiological vessels of humans or animals, according to an embodiment of the present disclosure.

FIG. 6 is a block diagram illustrating a system 400 for restricting fluid flow in physiological vessels of humans or animals, according to an embodiment of the present disclosure. Referring to FIG. 6, the system 400 comprises a plurality of the nanobots 100 described above; a power source 410 for powering the nanobots 100; and a controller 420 comprising one or more processors 425 for controlling the nanobots 100. The nanobots 100 are configured to be injected into a subject 430.

The power source 410 may comprise a magnetic flux generating mechanism for powering the nanobots 100, comprising a plurality of electrically isolated electromagnets, wherein the nanobots 100 are powered via a plurality of overlapping magnetic fields which are generated from the electrically isolated electromagnets.

Figure 7:
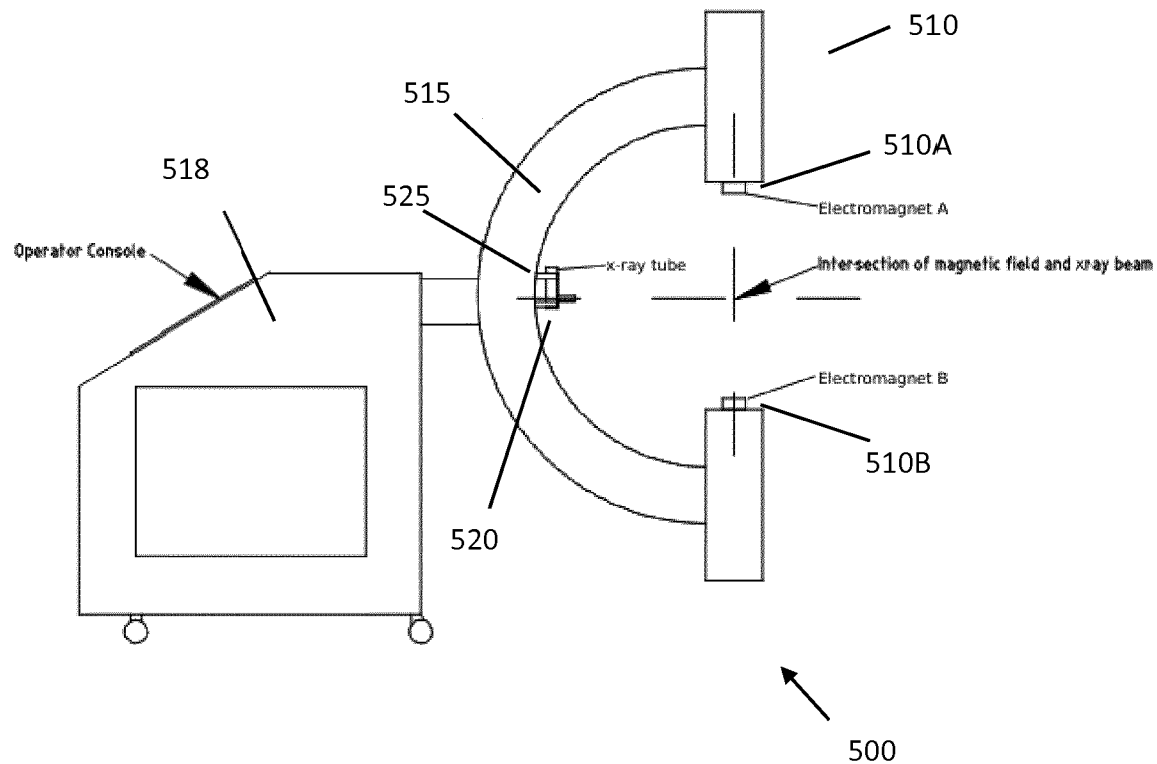
FIG. 7 illustrates a system for restricting fluid flow in physiological vessels of humans or animals, including a magnetic flux generation mechanism and an external beam radiation device, according to an embodiment of the present disclosure.

FIG. 7 illustrates a system 500 for restricting fluid flow in physiological vessels of humans or animals, including a magnetic flux generation mechanism 510 and an external beam radiation device 520, according to an embodiment of the present disclosure. Referring to FIG. 7, the magnetic flux generation mechanism 510 comprises two electromagnet assemblies 510A and 510B which are disposed to be opposite each other on a C-shaped assembly 515. In a variation on this embodiment, a single electromagnet assembly may be opposed by a counter mass for weight. The external beam radiation device 520 includes a radiation source comprising an X-ray tube 525. The magnetic flux generation mechanism 510 may also comprise an operator console 518 for operating the magnetic flux generation mechanism 510.

The electromagnet assemblies 510A and 510B may be constructed as described in U.S. Pat. No. 5,929,732 which describes a device for focusing a magnetic field. Using the mechanism described therein, the magnetic field from the primary magnet may be compressed into a small area thereby creating a high density magnetic field that extends in a beam-like manner from the electromagnet.

The X-ray tube 525 may be fitted with a collimator to ensure that the emerging X-ray beam is collimated and can overlap with the magnetic field generated. At the point where the x-ray beam and the focused magnetic field overlap, the conditions exist for the nanobot to be activated.

Figure 8:
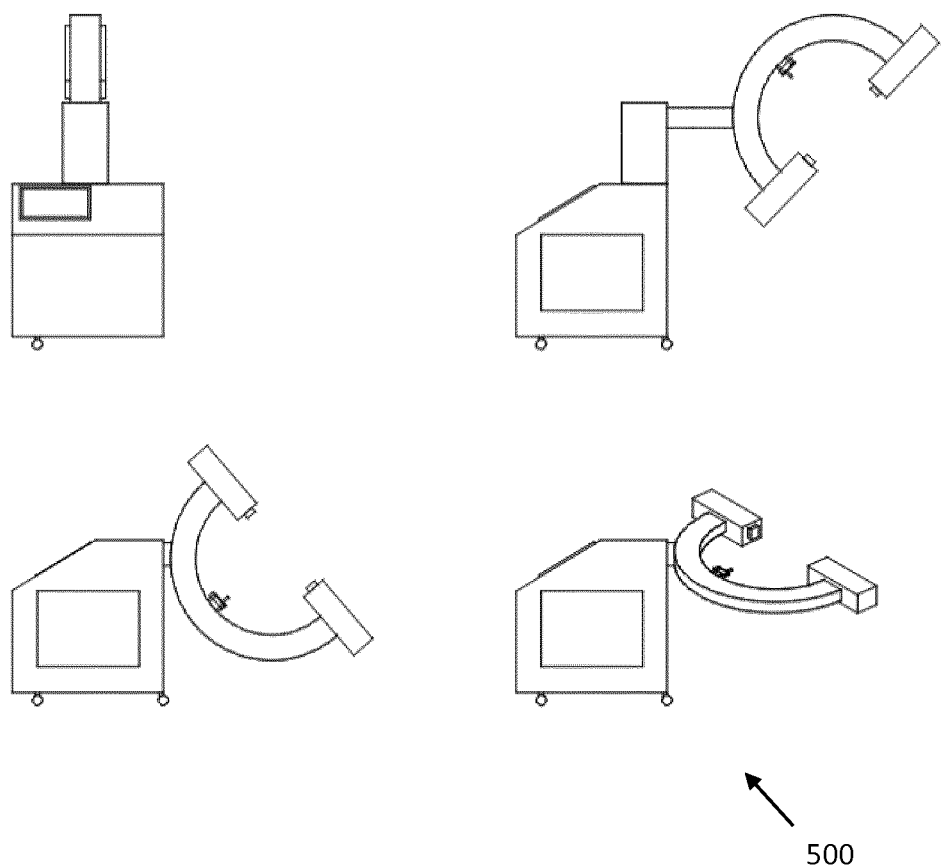
FIG. 8 illustrates the system of FIG. 7 in various configurations, according to an embodiment of the present disclosure.

During treatment the magnetic flux generating mechanism 510 may be configured to be moved via the operator console 518, as illustrated in FIG. 7, so that the intended focal point of the X-ray beam and magnetic field is located inside the tumour or target region. Once the nanobots are injected into the patient, they travel around the body and are activated inside the focal point of the X-ray beam and magnetic field. After a predetermined time, the magnetic flux generating mechanism 510 may be driven according to the operator's instructions so that the focal point is driven around the interior of the tumour or target region. When treatment is completed both the X-ray source and electromagnets 510A and 510B may be powered down. It may be that the treatment is repeated without the X-ray source to ensure that any remaining actuated nanobots may be reset to the unactivated state. FIG. 8 illustrates the system 500 in various configurations, according to an embodiment of the present disclosure.

Figure 9:
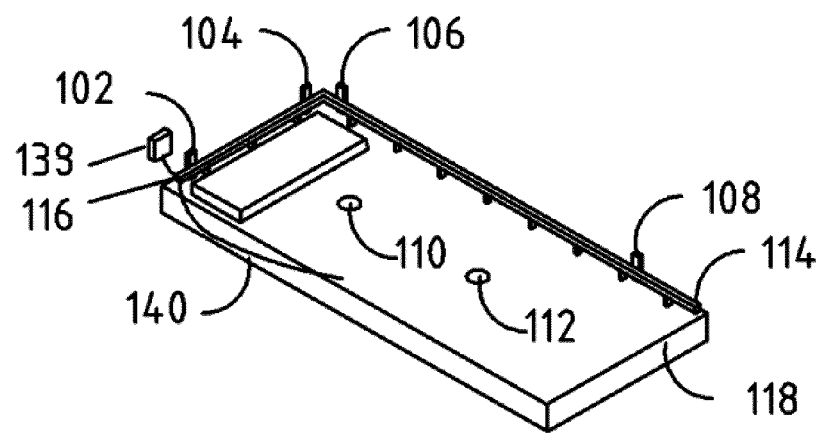
FIG. 9 illustrates the layout of a Primary Validation Sub-system (PVS) together with X, Y and Z Radio Frequency (RF) transmitters as they are located on a subject support, according to an embodiment of the present disclosure.
Figure 9:
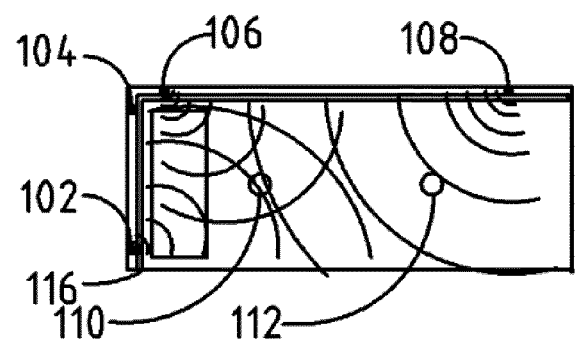
Figure 9:
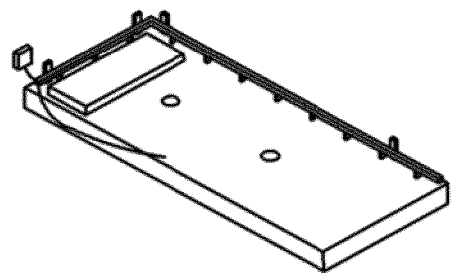
Figure 12:
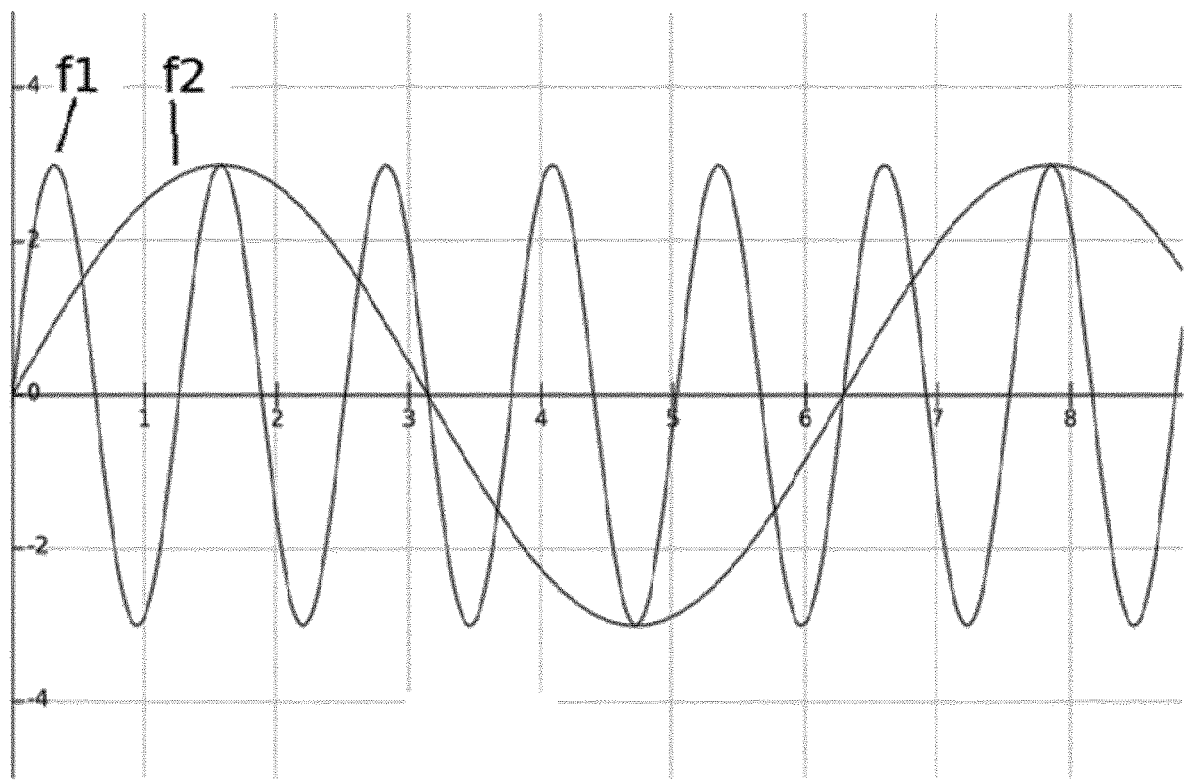
FIG. 12 shows the relationship between the f1 and f2 RF signals, the difference in position of wavefront peaks are used by the nanobot to determine its displacement from the initialiser, according to an embodiment of the present disclosure.
Figure 13:
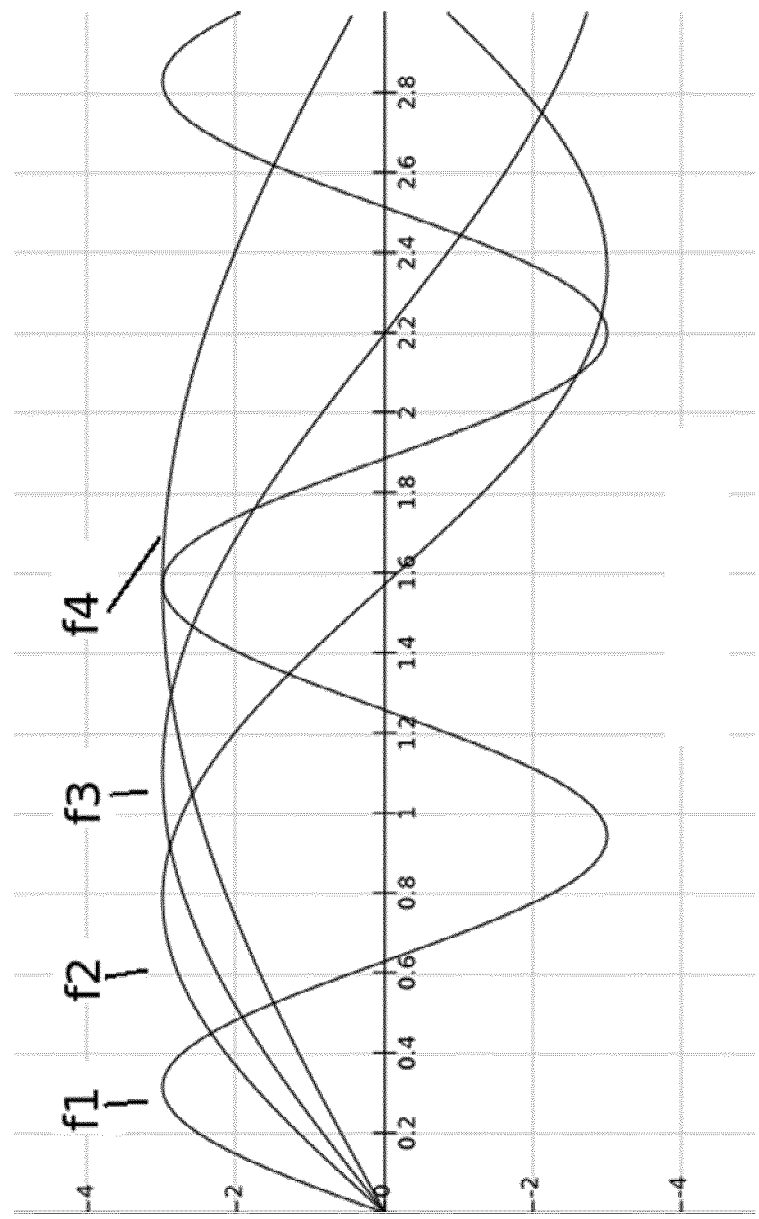
FIG. 13 shows example f1, f2, f3 and f4 signals as used by the PVS.

The system of the present disclosure may comprise a Primary Validation Sub-system (PVS). The PVS has two functions, 1) to provide a method by which the nanobots can measure their position inside a subject, and 2), a capability by which the nanobots can measure, calibrate and validate their positions prior to being injected into the subject. Referring to FIG. 9, the PVS may comprise a patient or subject support 118 comprising X, Y, and Z axes. A plurality of radio frequency (RF) transmitters may be provided on each of the X, Y, and Z axes. For example, the subject support 118 may comprise 6 RF transmitters comprising two X transmitters 102, 104, two Y transmitters 106, 108 and two Z transmitters 110, 112. Each of the RF transmitters may be configured to transmit at four wavelengths, referred to as f1, f2, f3 and f4. Each axis may have assigned a unique wavelength for f1, f2, f3 and f4 so that the nanobot can receive position information for each axis independently of the other axes. The wavelengths of f1, f2, f3 and f4 may be selected so that there is a sufficient difference between the fundamental wavelength of each of the signals to enable the measurement and correction of refractive error. The four wavelengths may be selected from as far across the selected RF spectrum as possible. The difference between the wavefronts of f1 and f2, illustrated in FIG. 12, may be used to determine displacement of the nanobot 100 relative to initialisation coordinates of the nanobot 100. The initialisation coordinates of the nanobot 100 may be located on X, Y, and Z axes of the subject support 118. In an ideal system, using f1 and f2 would be sufficient to accurately measure displacement relative to the initialisation coordinates. However, since the nanobots 100 may be used in a human or animal patient, it can be expected that refractive errors may occur due to the RF signals passing through bone, muscle and other body tissues. To compensate for this error, two additional wavelengths may be added, namely f3 and f4. Since refraction may affect different wavelengths in different ways (i.e. the error would be different on each wavelength) the difference measured between f2 and f3 and f2 and f4, as illustrated in FIG. 13, compared with the expected values in an errorless system, may be attributed to refractive error. This can then be measured and compensated in the on-board processor 130 of the nanobot 100. Two transmitters may be provided for each axis, and the on-board processor 130 of the nanobot 100 may obtain its actual location in said axis by triangulating the signals received from each transmitter and calculating true offset from the initialiser 116.

Figure 10:
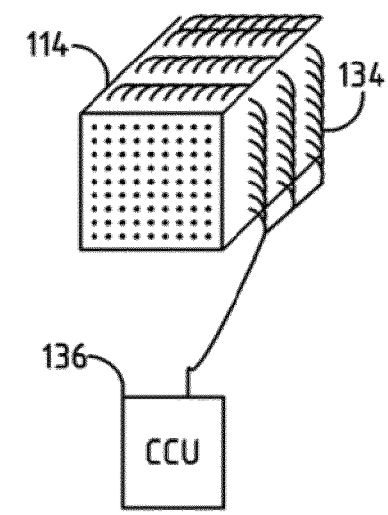
FIG. 10 illustrates an initialiser as it is installed with a capillary tube network of the Primary Validation Sub-system (PVS), according to an embodiment of the present disclosure.
Figure 10:
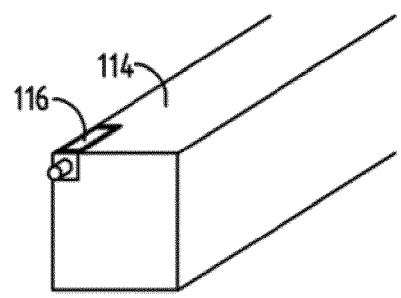
Figure 11:
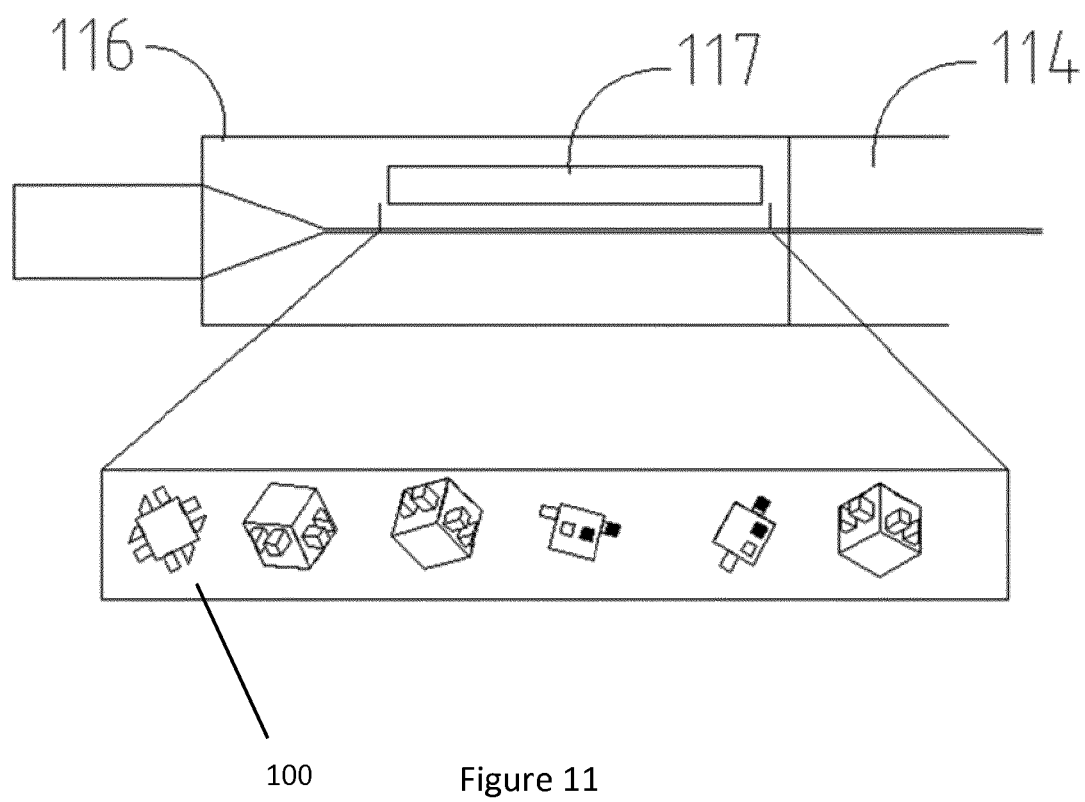
FIG. 11 shows an internal view of the initialiser together with its light sources and a blown-up view of nanobots travelling through the capillary network during initialisation, according to an embodiment of the present disclosure.

The PVS may also be configured to validate that the system is calibrated correctly and accuracy maintained prior to the nanobots 100 being administered to a subject. To this end the nanobots 100 may be expanded and viewed by a camera system during transformation from their unactivated state to expansion state to ensure expansion occurs at the intended location. For this reason, and referring to FIGS. 9 and 10, a capillary tube network 114 may be configured to run the width and length of the subject support 118. The capillary tube network 114 may comprise glass capillaries. An initialiser 116 may be disposed at one of the subject support 118. FIG. 11 illustrates an internal view of the initialiser 116 together with light sources and a blown-up view of nanobots 100 travelling through a capillary tube 114 during initialisation, according to an embodiment of the present disclosure. Referring to FIG. 10, the capillary tube network 114 may have fibre optics 134 attached at various points across the network 114 that connect to a camera control unit (CCU) 136 so that the nanobots can be viewed while being tested before being injected into the subject. The purpose of this is to verify using the CCU 136 that the nanobots can be expanded inside the capillary tube network at designated points. This ensures the correct and accurate operation of the nanobots and provides a method of calibration in the event that an inaccuracy is detected. Referring back to FIG. 9, also shown is a vessel 139 for mixing the nanobots with a solution, such as a saline solution, to enable both injection 140 of the nanobots into a patient and to aid their movement through the capillary tube network 114.

The system of the present disclosure may also comprise a Secondary Validation Sub-system (SVS). The SVS is configured such that the location of the tissue to be destroyed can be validated to verify the intended location as derived from initial subject scan data. To this end, as mentioned above, and referring to FIG. 3, each of the nanobots 100 may comprise a transmitter 128. The transmitter 128 may be provided on an outer surface of the main body 120 of the nanobot 100. The transmitter 128 may comprise an ultrasonic transmitter 128. The transmitter 128 may be configured to transmit an ultrasonic signal when the nanobot 100 enter within coordinates of the target region. The coordinates of the target region may be defined as offsets from the initialisation coordinates of all axes. Once the nanobots 100 have had time to make their way around the patient's circulatory system, targeting information may be transmitted by a controller to all of the nanobots 100 within range. If the nanobot position as measured by the nanobot 100 itself falls within the range of X, Y & Z coordinates of the target region as received, the nanobots 100 may start to emit a signal from the transmitter 128. In this configuration, it will be understood that the nanobots 100 are operating in their emitting mode. In their emitting mode, the one or more extending elements 122 may not be extended; rather they will vibrate to generate the ultrasonic signal. Thus, in their emitting mode, the nanobots 100 may be configured in the first cross-sectional size. The signal may be configured to be received by a suitably configured receiver and analysed accordingly. The SVS may thus be used to ensure that the intended target is treated and not an unintentional area.

The nanobots 100 may also generate an ultrasonic signal from the one or more extending elements 122. The one or more extending elements 122 may comprise a dense material such as Ruthenium in order to increase ultrasonic output. The main body 120 may be configured to be lighter than the one or more extending elements 122. The main body 120 may comprise silicon. If the nanobots 100 start to extend and retract the one or more extending elements 122 to generate a signal, the main body 120 which may be configured to be lighter than the one or more extending elements 122 will move. To generate the ultrasonic signal, the one or more extending elements 122 may be extended and retracted at several kilohertz over a very short distance. Since the one or more extending elements 122 may be heavier than the main body 120, the main body 120 will tend to move so the entire outside surface of the nanobot 100 can be used to generate the signal. In this way the entire side of the nanobot 100 may be configured to function as a speaker (Newton's third law).

Another use for the SVS is to use the signal transmitted from inside blood vessels for the purpose of measuring the rate of blood flow and to enable imaging of blood vessels from inside the vessels themselves. As mentioned above, the signal transmitted by the nanobots may comprise an ultrasonic signal. Conventionally, ultrasonic receivers both transmit an ultrasonic signal and then receive and interpret the reflected signal. Transmitting an ultrasonic signal from within a subject instead of from an external transmitter enables ultrasonic imaging from within the target region, thereby reducing the amount of unwanted ultrasonic reflections during a patient scan. Since the source of the ultrasonic emissions is known accurately via the PVS coordinates and the time of flight is known, it can be accurately predicted how long the signal should take to travel from the target region to the sensor. Since reflections will have a longer path than direct signals, they can easily be identified and either ignored or used for off location imaging. In this regard, if a signal is bounced off a nearby organ, the reflected signal will take longer to reach the sensor; however this reflected signal may also be used for imaging too. For example if the ultrasonic source is inside a large tumour, the reflection data may provide more details about the outside surface shape of the tumour).

Figure 14:
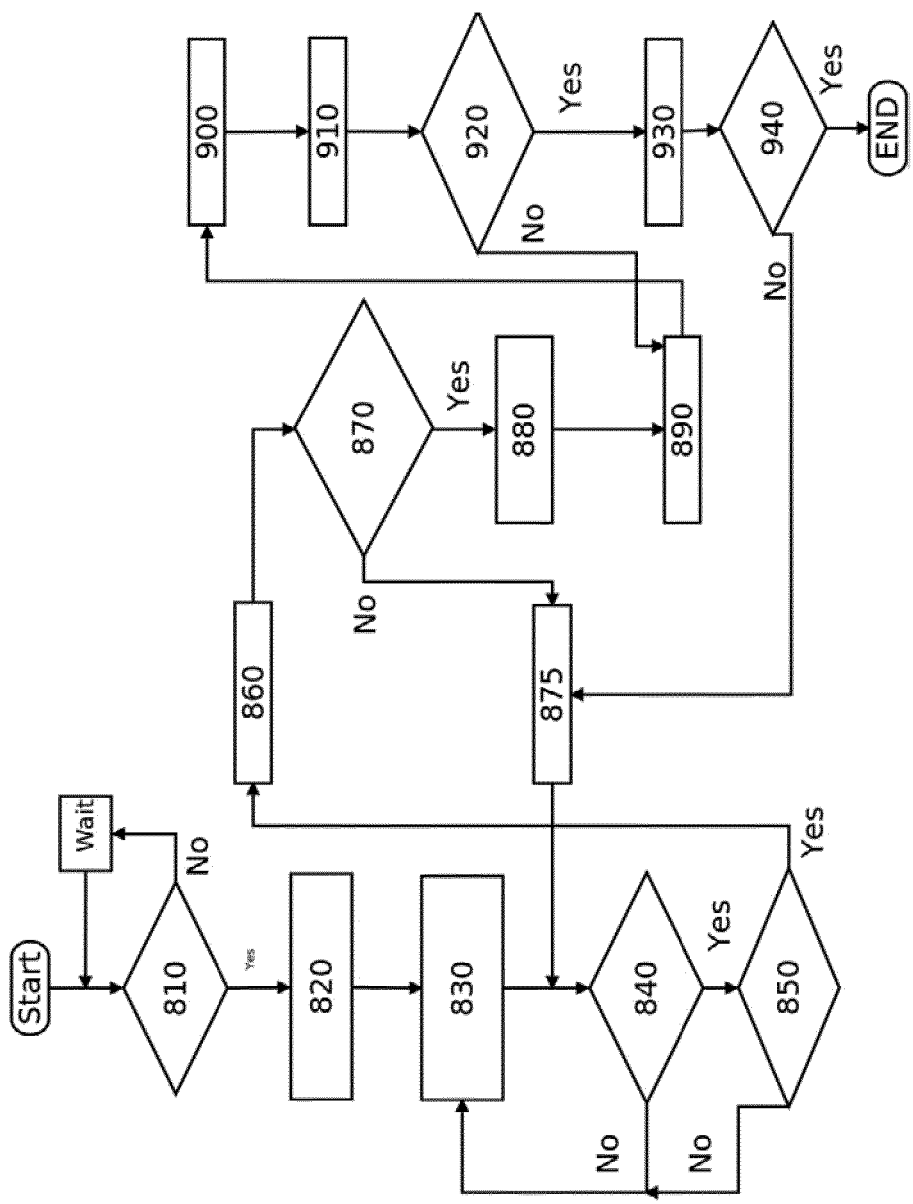
FIG. 14 is a flowchart illustrating a method of controlling operation of the nanobots, according to an embodiment of the present disclosure.

FIG. 14 is a flowchart illustrating a method of controlling operation of the nanobots, according to an embodiment of the present disclosure. Steps of the method may be performed by the controller 420 illustrated in FIG. 6. Referring to FIG. 14, the method may comprise initialising the nanbots 810. As described above and as illustrated in FIGS. 9 to 11, the nanobots 100 may be initialised in the initialiser 116. In an embodiment, the nanobots 100 may pass in front of an optical transmitter which emits light of high intensity from the light source 117. The nanobot 100 may comprise an onboard optical sensor 124 to detect the light irradiated by the light source 117. By passing by the initialiser 116, the nanobot 100 may detect first an increased voltage from the optical sensor 124 as it passes the light source 117 and then a reduction in voltage as it leaves the initialiser 116. The method may comprise acquiring X, Y and Z RF signals and setting the coordinates of the nanobots to zero 820. Then a count of fringes from RF frequencies for all axes is performed to determine the relative position of the nanobots from the initialisation coordinates 830. Coordinates of a target region may then be sent to the nanobots. It may then be determined whether coordinates of the target region have been received by the nanobots 840. If the coordinates of the target region have been received by the nanobots, the nanobots may determine if their current coordinates are within the coordinates of the target region 850. The coordinates of the target region 850 may be user-defined. If the current coordinates of the nanobots are within the coordinates of the target region, the onboard transmitter may be configured to transmit a signal 860. In this configuration, it will be understood that the nanobots 100 are operating in their emitting mode. In their emitting mode, the one or more extending elements 122 of the nanobots may not be extended. It may then be determined whether the signal has been received from the target region 870. If a signal has been received from the target region, an activation signal may be sent to the nanobots in the target region 880. If it is determined that the signals have been received from an area other than the target region, an offset may be added to the coordinates of the target region 875. A new target region may be defined by applying an offset to the coordinates of the target region. One reason this may happen is when targeting a lung tumour as a lung tumour always moves with breathing; this can also be true for tumours of the digestive system. Once the activation signal is received by the relevant nanobots, the nanobots in question may be activated to their expanded mode as described above 890. In the context of deployment in human or animal tissue, the activation of the nanobots to their expanded mode in the target region disrupts fluid flow in the blood vessels 900 which may cause the tissue in the vicinity to die 910. A deactivation signal may be sent to the relevant nanobots 920 to cause the extending elements of the nanobots to retract. It may be finally determined whether the treatment is complete 940.

As an alternative to the Secondary Validation Sub-system (SVS) described above, an ultrasonic imaging system may be employed, according to an embodiment of the present disclosure. The nanobots described above may be the ultrasonic imaging source. As mentioned above, the nanobots may comprise an ultrasonic transmitter for emitting ultrasonic signals. Transmitting an ultrasonic signal from nanobots within a subject enables ultrasonic imaging from within the target region. The ultrasonic imaging system removes the need for the external calibration of the nanobots, thereby obviating the need for the cameras, capillary tube network and fiber optics that run around the subject support. The ultrasonic imaging system also removes the need for a CT scan or MRI for imaging prior to treatment so that the system can be used for preventive medicine. The ultrasonic imaging system requires both the nanobots and the PVS to work. The ultrasonic imaging system may be used for patient check-ups as follows. A patient may go to the ultrasonic imaging system, lie down and be injected with nanobots. The system may be configrued to perform a full check-up of vital organs including angiograms (to check for potential artery blockage, etc). The ultrasonic imaging system is configured to acquire a higher quality image than other diagnostic systems in real time. Small cancer tumors are usually very difficult to detect. In the ultrasonic imaging system according to the present embodiment, cancer tumors will show up brightly in the scan due to the fact that cancer has more blood vessels than surrounding tissue. If these tumors are detected, they can be destroyed at the time of diagnosis so that the cancer may be eradicated quickly.

Figure 15:
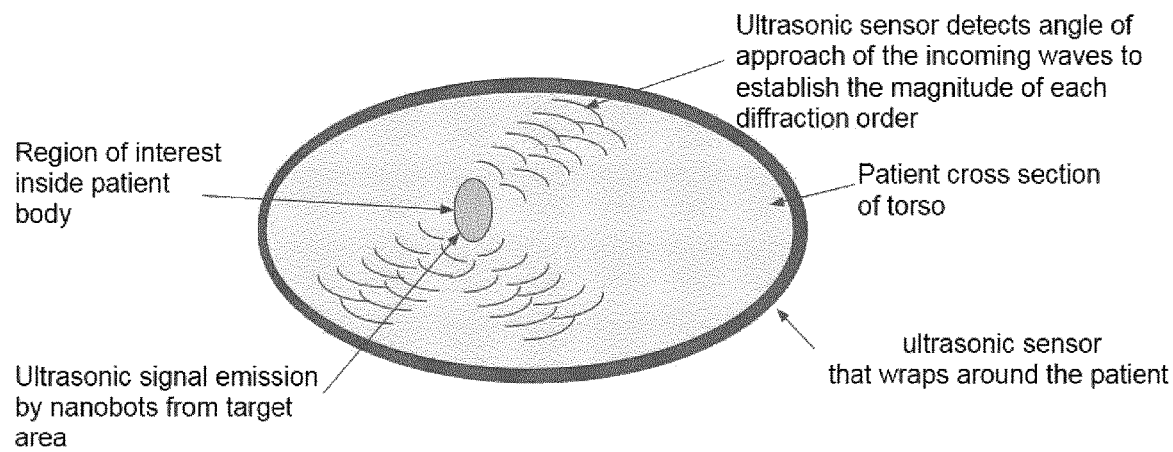
FIG. 15 is a diagram illustrating an ultrasonic imaging system according to an embodiment of the present disclosure.
Figure 20:
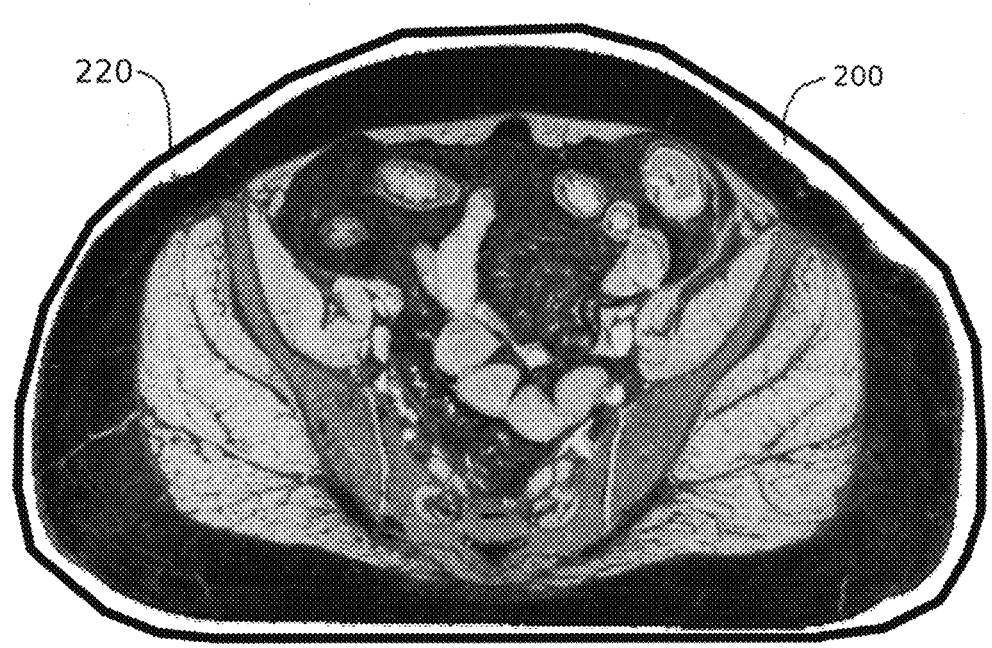
FIG. 20 illustrates a fabric with an embedded UDM matrix wrapped around a human pelvis with an ultrasonic gel between the patient's body and the UDM matrix to prevent attenuation of the ultrasonic waves, according to an embodiment of the present disclosure.

The present embodiment comprises a system for converting ultrasonic signals and diffraction orders into an optical image using a network of sensors embedded across the surface of a fabric or other material. This can be referred to as an ultrasonic detection matrix. The ultrasonic detection matrix may be configured to be wrapped around a subject or patient's body so that the sensors are in contact with the outer surface of the subject or patient's body, as illustrated in FIGS. 15 and 20. In this manner, refracted and reflected waves can be detected in any angle up to 360 degrees with respect to any axis (sagittal plane, transverse plane or coronal plane). Because of this, any ultrasonic waves generated in the space inside the fabric (or inside the patient) can be detected. More specifically, in the context of the present disclosure, ultrasonic signals generated by the nanobots inside the subject or patient can be detected. Indeed all diffraction orders can be acquired in this way and the ultrasonic detection matrix may be configured to detect the angle of incidence of the ultrasonic waves and together with time domain tracking of the measured signals, it may be configured to establish what order was detected and the angle of detection as well as intensity. In this manner it is possible to suppress the effect of the zero and lower orders when desired while processing high order information, resulting in superior real-time imaging performance.

In traditional imaging systems it is necessary to combine the zero order wave with higher orders to form an image on a plane. This concept limits the imaging capability of the imaging system as there is a physical limit on the possible incoming or outgoing angle of light. The system of the present disclosure does not attempt to reform the orders into a coherent image. Instead the system can detect the angle of incidence of the diffraction order as well as its intensity. A controller comprising one or more processors can process the data from the ultrasonic detection matrix to build an image electronically. An advantage of this method is that it is possible to electronically reduce the effect of the zero order as well as the lower orders with respect to the intensity of the higher orders which can now be amplified. Also since the incoming diffraction orders do not need to be recombined physically, the depth focus of the system is independent of numerical aperture (NA) and in fact the NA is also practically above unity, meaning with enough processing power, an entire human body can be imaged and held in focus simultaneously in very high resolution.

The present disclosure provides an ultrasonic imaging system using an externally produced ultrasonic signal as an illumination source. For example, and in the context of the present disclosure, highly accurate blood borne nanobots as described above may be used to generate the ultrasonic signal. Since all tissue in the human body requires a blood supply, this method when coupled with an accurate guidance system for the nanobots, provides for great flexibly in the location of the ultrasonic sources.

In order to accurately image, the system uses a "time-of-flight" method as one variable to form an image. The time-of-flight concept is used quite frequently in ultrasonic imaging as it is based on the difference between the time that the ultrasonic signal is transmitted from the transmission location and when it is received by the receiver. From the measurement of this time, the total distance travelled by the ultrasonic wave can be measured and from that, the location from which the wave has been reflected or refracted can be calculated. The ultrasonic imaging method of the present embodiment provides for the ability to measure the angle of the incoming wave as well as its intensity. FIG. 15 shows how this is achieved.

Figure 16:
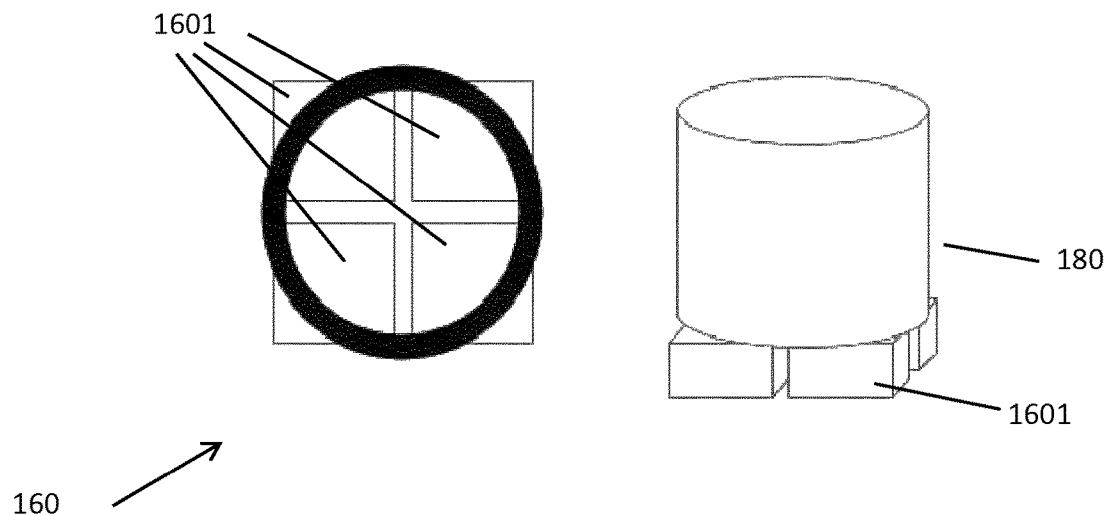
FIG. 16 illustrates plan and perspective views of a single ultrasonic detection module (UDM), according to an embodiment of the present disclosure.

More specifically, FIG. 16 illustrates plan and perspective views of a single ultrasonic detection module (UDM) 160, according to an embodiment of the present disclosure. Referring to FIG. 16, the single UDM 160 comprises an assembly of piezo-electric elements configured to convert the ultrasonic signals into electrical signals. This single UDM 160 may comprise a plurality of piezo-electric sensors 1601 upon which is mounted a rigid column 180. The rigid column 180 may be configured to be both rigid and have a low mass (to avoid resonance). The rigid column 180 may comprise a material such as carbon fibre or carbon nanotubes. The rigid column 180 may comprise a ceramic material. The rigid column 180 may be cylindrical as it is the most efficient shape. Other shapes may be used, but correction factors would need to be applied to the signals.

Figure 17:
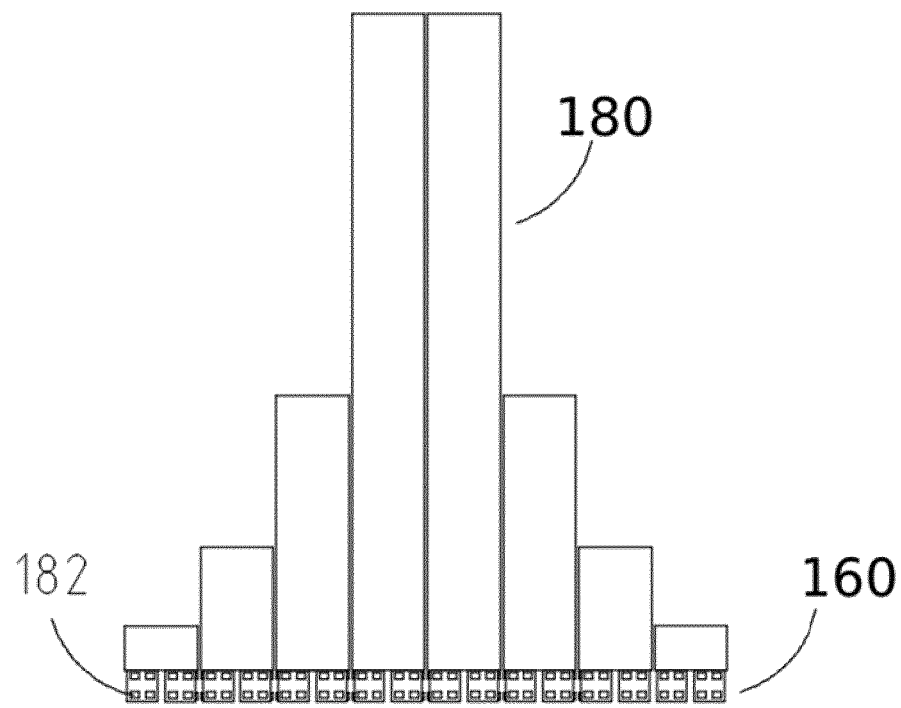
FIG. 17 is an elevation view of a single ultrasonic detection assembly (UDA); according to an embodiment of the present disclosure.
Figure 18:
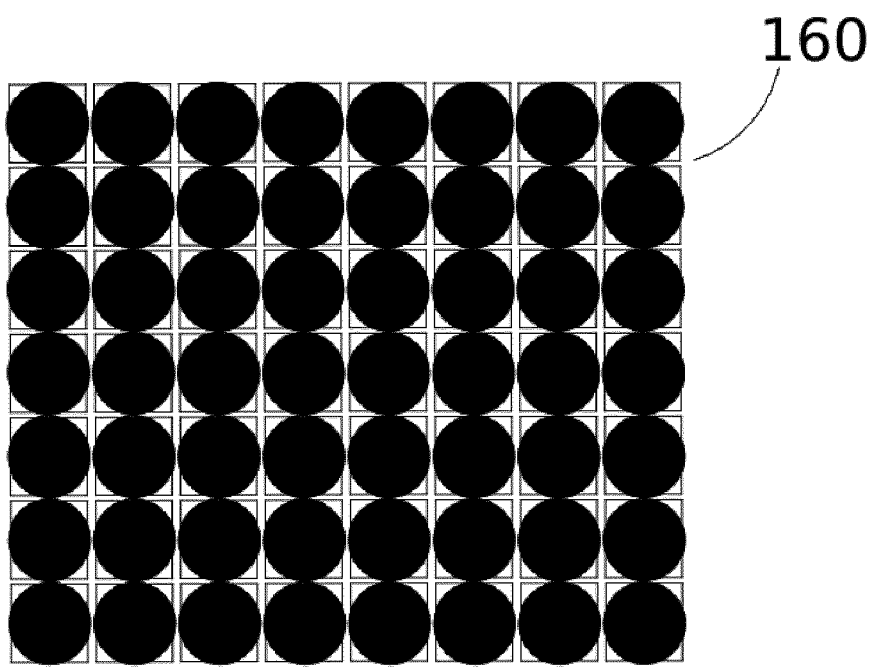
FIG. 18 is a plan view of a single ultrasonic detection assembly (UDA) together with its associated rigid column assembly, according to an embodiment of the present disclosure.

Together the piezo-electric sensors 1601 and the rigid column 180 constitute a single ultrasonic detection module (UDM). Referring to FIGS. 17 and 18, a large number of UDMs may be mounted to cover the surface of a fabric or material that can be wrapped around a patient. In this manner, a rigid assembly may be formed on top of the piezo-electric assembly comprising individual columns of different heights and may be assembled together into a unit called an ultrasonic detection assembly (UDA). An ultrasonic detection assembly (UDA) comprises a plurality of UDMs, with the rigid column of each UDM being of different height to other UDMs across the UDA. In this manner, a single UDA may be thought of as being similar to a camera pixel except instead of detecting colour, a UDA can detect the angles of the incoming diffraction orders as well as their intensity and can differentiate the intensity of the different orders. Each of the UDMs has a rigid column of a different height so that columns near the centre of the UDA are highly sensitive to diffraction orders with a high angle (as they are low power but contain detailed information about the source). Due to this configuration, it is possible to electronically subtract the zero order (which contains a lot of energy but no information) and amplify the higher orders (unlike conventional imaging systems which are the opposite, such as a camera lens).

Referring to FIG. 17, the UDM 160 may include one or more displacement sensors 182, such as a capacitance gauge, to measure the relative offset between each UDM. In other embodiments, it may not be necessary to put displacement sensors on each UDM but on each UDA for simplicity.

Figure 19A:
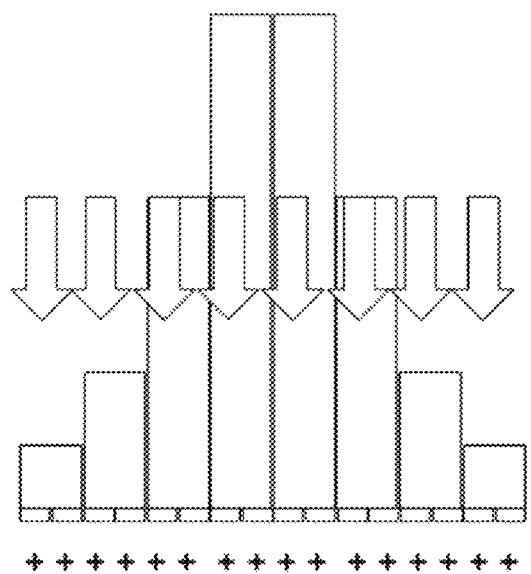
FIGS. 19a and 19b illustrate ultrasonic waves incident on the ultrasonic detection assembly (UDA) of FIG. 17.
Figure 19B:
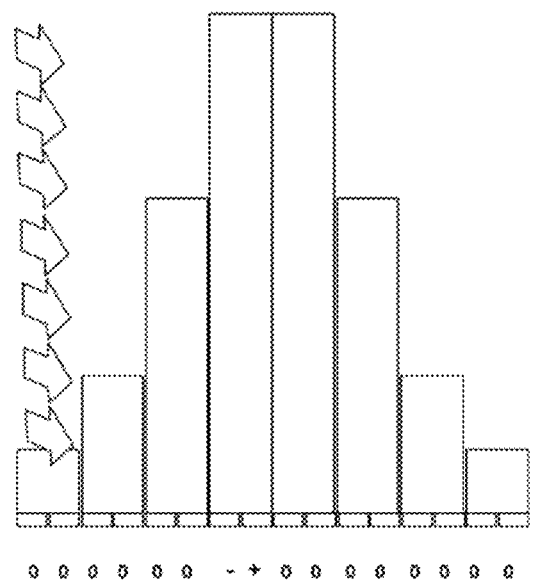

The differentiation of the diffraction orders may be achieved as follows. FIG. 17 illustrates an elevation view of a single ultrasonic detection assembly (UDA), according to an embodiment of the present disclosure. FIG. 18 illustrates a plan view of a single UDA 160 together with its associated rigid assembly, according to an embodiment of the present disclosure. Note in FIG. 17 that the individual columns 180 increase in height toward the centre of the assembly. Referring to FIG. 19a, in the event that a wave approaches orthogonal to the upper surface of the piezo-electric sensors, a voltage will be generated in the piezo-electric sensors 1601 and if the approaching wave is orthogonal, the voltage generated by the piezo-electric sensors 1601 will be equal across all the piezo-electric sensors 1601. If however, referring to FIG. 19b, a wave approaches at an angle to the rigid column 180, the voltage generated by the piezo-electric sensors 1601 will not be equal across all the piezo-electric sensors 1601 since there will be a lateral force on the rigid column 180 which will be transferred to the piezo-electric sensors 1601 below. Any difference in the voltage generated across all the piezo-electric sensors 1601 will correspond to an angular component of the arriving wave. The difference in strain measured by the different piezo-electric sensors 1601 is proportional to the direction of the incoming wave. Using this method coupled with the already mentioned time-of-flight method, the energy and direction of the incoming wave can easily be calculated as well as the image location.

The height of the rigid column 180 determines the sensitivity of the ultrasonic detection module (UDM) to angular component detection. For this reason a number of UDMs may be assembled together with rigid columns of different heights in order to improve detection capabilities for higher diffraction orders. By subtracting the voltages from the piezo-electric sensor assembly from a single UDM from its neighbour with a higher rigid column, the energy from a lower diffraction order can be calculated even if it approaches the detector at the same angle.

It can be seen in FIG. 15 that this configuration allows the detection of waves that travel parallel to the surface of the sensors embedded into the fabric. For high resolution imaging the lower orders can be electronically attenuated and higher orders amplified when desired in order to achieve the optimum image quality in real time.

Also, the desired image data from the intended target region can be acquired and unwanted reflections can easily be identified (using time-of-flight data together with the measurement of angle of arrival and signal intensity) and removed where desired or indeed reused when desired since it is possible to discern what is usually undesirable reflected waves and use these as a secondary ultrasonic illumination source where applicable. By reusing what has traditionally been considered to be noise (because the entire history of the wave can be obtained from its time-of-flight data as well as its intensity and angle of approach as well as intensity) the system can provide diagnostic options previously unavailable in the field of ultrasonic imaging.

As the system has no real image plane in the traditional sense (as the diffraction orders are not reassembled by the imaging detection mechanism but rather digitally by a computer) depth of focus is no longer a consideration since the diffraction orders may be measured by the image detection mechanism and then assembled and modeled mathematically by computer.

The UDAs may be attached to a substrate material. The substrate material may comprise a flexible membrane such as cotton or rubber or other such material such that the UDAs can move relative to each other. FIG. 20 illustrates a fabric with an embedded UDM matrix 220 wrapped around a human pelvis with an ultrasonic gel 200 between the patient's body and the UDM matrix to prevent attenuation of the ultrasonic waves, according to an embodiment of the present disclosure. Since the substrate material is flexible, sensors (such as capacitive sensors or other such sensors) can measure the relative offset between each UDA. The purpose of this is to measure the deviation in the detection plane caused by variations in the patient's body profile. This data is necessary to interpolate the ultrasonic signals received as the detector distance from the emitter must be known in order for the time-of-flight data to be useful.

The substrate material may have different forms to best suit the patient body profile. In some cases this may involve using a custom suit (for example, a diving or scuba suit) to bring as much of the patient's outer body into contact with the detection mechanism. The inside of the suit may be lined with UDMs and the suit forms the "base" shape. When the patient wears the suit, it will form around the patient and the difference between the default shape and the patient shape can be measured using the displacement sensors of the UDMs. At the start of a procedure, the displacement sensors 182 may be configured to be reset from a known reference. In the case of a flat detector, the detector may be rolled flat and the sensors initalised for the known (flat) reference. In the case of a full body detector, the suit may be mounted first on a mannequin or other such known reference for resetting. In this manner, any differences in body profile between the patient and the reference can be measured and corrected for.

The ultrasonic imaging system according to the present embodiment may be employed to obtain high definition images in real time using ultrasound. Since the source of the signal can be know accurately, all reflections normally considered to be noise in conventional ultrasound diagnostics can be used as an additional illumination source (since time-of-flight data and location of the sources is always known). Depth of focus is not a consideration since the image can be constructed digitally by recombining the diffraction orders in a virtual environment instead of a physical imaging system.

Figure 21:
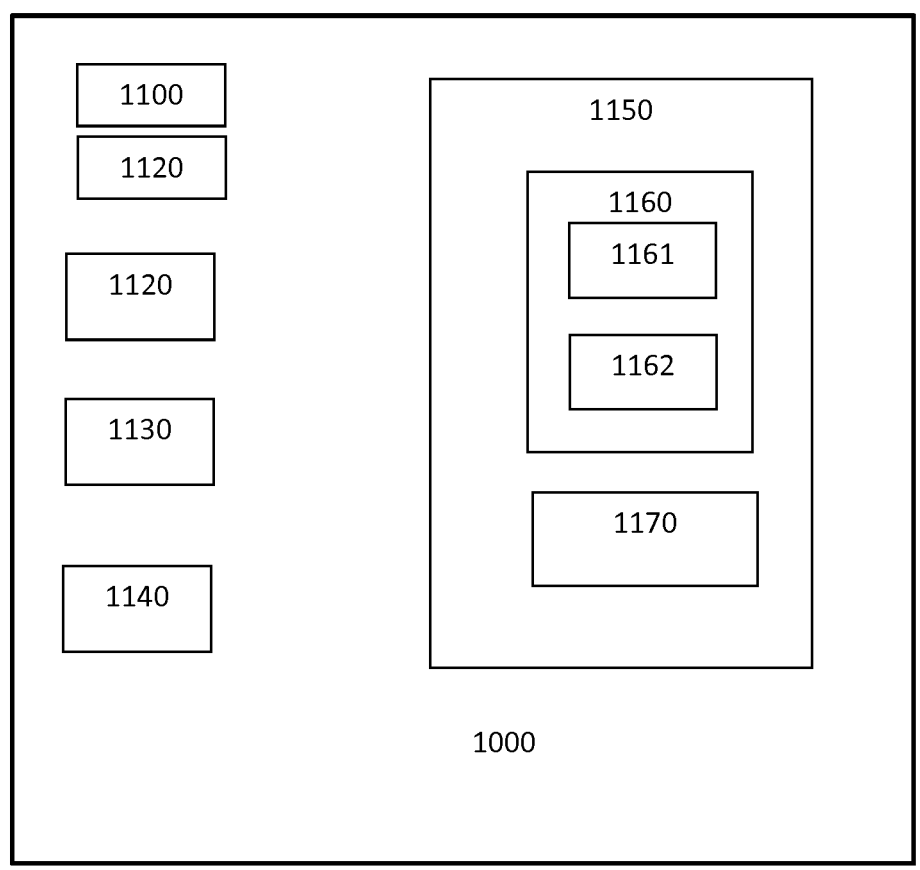
FIG. 21 is a block diagram illustrating an exemplary configuration of a computing device comprising various hardware and software components that function to perform processing steps according to embodiments of the present disclosure.

FIG. 21 is a block diagram illustrating a configuration of a computing device 1000 according to an embodiment of the present disclosure. The computing device 1000 includes various hardware and software components that function to perform processing steps such as the primary validation, secondary validation, and ultrasonic imaging according to embodiments of the present disclosure. Referring to FIG. 21, the computing device 1000 comprises a user interface 1100, a controller 1120 in communication with a memory 1150, and a communication interface 1130. The controller 1120 may comprise the controller described above for controlling the nanobots. The controller 1120 may be configured to: receive coordinates of a plurality of nanobots in a subject; compare coordinates of a target region with the coordinates of the nanobots; determine which of the nanobots are located in the target region; and activate nanobots located in the target region. The controller 1120 may also be configured to receive signal data received at the ultrasonic detection matrix to generate an image of a subject, the signal data comprising diffraction orders corresponding to ultrasonic signals emitted by the nanobots. The controller 1120 functions to execute software instructions that can be loaded and stored in the memory 1150. The controller 1120 may include a number of processors, a multi-processor core, or some other type of processor, depending on the particular implementation. The memory 1150 may be accessible by the controller 1120, thereby enabling the controller 1120 to receive and execute instructions stored on the memory 1150. The memory 1150 may be, for example, a random access memory (RAM) or any other suitable volatile or non-volatile computer readable storage medium. In addition, the memory 1150 may be fixed or removable and may contain one or more components or devices such as a hard drive, a flash memory, a rewritable optical disk, a rewritable magnetic tape, or some combination of the above.

One or more software modules 1160 may be encoded in the memory 1150. The software modules 1160 may comprise one or more software programs or applications having computer program code or a set of instructions configured to be executed by the controller 1120. Such computer program code or instructions for carrying out operations for aspects of the systems and methods disclosed herein may be written in any combination of one or more programming languages.

The software modules 1160 may include programs configured to be executed by the controller 1120. During execution of the software modules 1160, the controller 1120 configures the computing device 1000 to perform various operations relating to the control of the nanobots according to embodiments of the present disclosure, as has been described above.

Other information and/or data relevant to the operation of the present systems and methods, such as a database 1170, may also be stored on the memory 1150. The database 1170 may contain and/or maintain various data items and elements that are utilized throughout the various operations of the system described above. The information stored in the database 1170 may include but is not limited to, patient information and MRI data. It should be noted that although the database 1170 is depicted as being configured locally to the computing device 1000, in certain implementations the database 1170 and/or various other data elements stored therein may be located remotely. Such elements may be located on a remote device or server—not shown, and connected to the computing device 1000 through a network in a manner known to those skilled in the art, in order to be loaded into a processor and executed.

Further, the program code of the software modules 1160 and one or more computer readable storage devices (such as the memory 1150) form a computer program product that may be manufactured and/or distributed in accordance with the present disclosure, as is known to those of skill in the art.

The communication interface 1140 is also operatively connected to the controller 1120 and may be any interface that enables communication between the computing device 1000 and external devices, machines and/or elements. The communication interface 1140 is configured for transmitting and/or receiving data. For example, the communication interface 1140 may include but is not limited to a Bluetooth®, or cellular transceiver, a satellite communication transmitter/receiver, an optical port and/or any other such, interfaces for wirelessly communicating between the computing device 1000 and the nanobots.

The user interface 1100 may be also operatively connected to the controller 1120. The user interface 1100 may comprise one or more input device(s) such as switch(es), button(s), key(s), and a touchscreen.

The user interface 1100 functions to allow the entry of certain information about the patient and activation/deactivation signals as discussed above.

A display may also be operatively connected to the processor 120. The display may include a screen or any other such presentation device that enables the user to view various options, parameters, and results. The display may be a digital display such as an LED display. The user interface 1100 and the display may be integrated into a touch screen display.

The operation of the computing device 1000 and the various elements and components described above will be understood by those skilled in the art with reference to the device and system for restricting fluid flow in blood vessels of humans or animals according to the present disclosure.

The words comprises/comprising when used in this specification are to specify the presence of stated features, integers, steps or components but does not preclude the presence or addition of one or more other features, integers, steps, components or groups thereof.

The invention claimed is:

1. A device for restricting fluid flow in physiological vessels of humans or animals, the device being configurable in a first mode to be propellable within a physiological vessel and in a second mode to at least partially occlude a physiological vessel, the device having a first cross-sectional size in the first mode and a second cross-sectional size in the second mode, wherein the second cross-sectional size is greater than the first cross-sectional size, wherein the device is configurable in the first mode to be passively propellable by fluid flow within a physiological vessel and in the second mode to at least partially occlude a capillary and to have the second cross-sectional size in a range of about 7.7 µm to about 14.3 µm, said device comprising:
   a main body; and
   one or more extending elements that extend from the main body to increase the cross-sectional size of the device when activated.

2. The device of claim 1, wherein the first cross-sectional size is in a range of about 2.8 µm to about 5.2 µm.

3. The device of claim 1, wherein the main body has a parallelpiped shape, wherein the one or more extending elements extend from at least one face of the main body.

4. The device of claim 1, comprising at least one of the following:
   a micromotor for driving the one or more extending elements;
   an optical sensor for initializing the device;
   an on-board processor for collecting and processing data.

5. A device for restricting fluid flow in physiological vessels of humans or animals, the device being configurable in a first mode to be propellable within a physiological vessel and in a second mode to at least partially occlude a physiological vessel, the device having a first cross-sectional size in the first mode and a second cross-sectional size in the second mode, wherein the second cross-sectional size is greater than the first cross-sectional size, wherein the device is configurable in the first mode to be passively propellable by fluid flow within a physiological vessel and in the second mode to at least partially occlude a capillary and to have the second cross-sectional size in a range of about 7.7 µm to about 14.3 µm, said device further comprising a transmitter for verifying the location of the device in the humans or animals.

6. The device of claim 5, wherein the transmitter comprises an ultrasonic transmitter.

7. A device for restricting fluid flow in physiological vessels of humans or animals, the device being configurable in a first mode to be propellable within a physiological vessel and in a second mode to at least partially occlude a physiological vessel, the device having a first cross-sectional size in the first mode and a second cross-sectional size in the second mode, wherein the second cross-sectional size is greater than the first cross-sectional size, wherein the device is configurable in the first mode to be passively propellable by fluid flow within a physiological vessel and in the second mode to at least partially occlude a capillary and to have the second cross-sectional size in a range of about 7.7 µm to about 14.3 µm, said device further comprising a coil for generating electrical power required to power the device from a magnetic field.

8. The device of claim 1, A device for restricting fluid flow in physiological vessels of humans or animals, the device being configurable in a first mode to be propellable within a physiological vessel and in a second mode to at least partially occlude a physiological vessel, the device having a first cross-sectional size in the first mode and a second cross-sectional size in the second mode, wherein the second cross-sectional size is greater than the first cross-sectional size, wherein the device is configurable in the first mode to be passively propellable by fluid flow within a physiological vessel and in the second mode to at least partially occlude a capillary and to have the second cross-sectional size in a range of about 7.7 µm to about 14.3 µm, said device further comprising a radiation sensitive device to enable the device to be activated by ionizing electromagnetic radiation.

9. The device of claim 8, wherein the radiation sensitive device comprises a diode or a photodiode.

10. The device of claim 8, wherein the radiation sensitive device comprises a transistor or a metal-oxide-semiconductor field-effect transistor (MOSFET).

11. The device of claim 8, wherein the radiation sensitive device is coated with a scintillating material.

12. A system for restricting fluid flow in physiological vessels of humans or animals, the system comprising:
   a plurality of devices for restricting fluid flow in physiological vessels of humans or animals, each device being configurable in a first mode to be propellable within a physiological vessel and in a second mode to at least partially occlude a physiological vessel, each device having a first cross-sectional size in the first mode and a second cross-sectional size in the second mode, wherein the second cross-sectional size is greater than the first cross-sectional size, wherein each device is configurable in the first mode to be passively propellable by fluid flow within a physiological vessel and in the second mode to at least partially occlude a capillary and to have the second cross-sectional size in a range of about 7.7 µm to about 14.3 µm;
   a power source for powering the plurality of devices; and
   a controller comprising one or more processors for controlling the plurality of devices.

13. The system of claim 12, wherein the power source comprises a magnetic flux generating mechanism for powering nanobots, comprising a plurality of electrically isolated electromagnets, wherein the plurality of devices are powered via a plurality of overlapping magnetic fields which are generated from the electrically isolated electromagnets.

14. The system of claim 12, comprising an external beam radiation device for producing a beam of ionizing electromagnetic radiation to illuminate tissue in a target region.

15. The system of claim 12, comprising a capillary tube network having fibre optics attached to a camera control unit so that the plurality of devices can be viewed while being activated before being injected into the humans or animals.

16. The system of claim 12, comprising an ultrasonic detection matrix for detecting ultrasonic signals generated from within the humans or animals.

17. The system of claim 16, wherein the ultrasonic detection matrix comprises:
- a flexible substrate material; and
- a plurality of ultrasonic detection assemblies (UDA) attached to the substrate material.

18. The system of claim 17, wherein each UDA comprises a plurality of ultrasonic detection modules (UDM) for detecting ultrasonic signals emitted by nanobots, each UDM comprising a rigid column disposed on a plurality of piezoelectric sensors.

19. The system of claim 18, wherein each ultrasonic detection assembly (UDA) comprises a plurality of UDMs arranged in an array, with the rigid column of each UDM being of different height to that of other UDMs.

* * * * *